United States Patent [19]

Fehr et al.

[11] Patent Number: 5,124,501
[45] Date of Patent: Jun. 23, 1992

[54] PROCESS FOR THE PREPARATION OF AN UNSATURATED POLYOLEFIN

[75] Inventors: Charles Fehr, Versoix; José Galindo, Les Avanchets, both of Switzerland

[73] Assignee: Firmenich SA, Geneva, Switzerland

[21] Appl. No.: 755,885

[22] Filed: Sep. 6, 1991

[30] Foreign Application Priority Data

Sep. 25, 1990 [CH] Switzerland .................. 3087/90

[51] Int. Cl.$^5$ .................. C07C 2/00; C07C 11/21
[52] U.S. Cl. ....................... 585/600; 585/638
[58] Field of Search ............. 585/600, 638, 639

[56] References Cited

U.S. PATENT DOCUMENTS 4,014,951  3/1977  Näf et al. .................. 585/600
4,642,692  3/1987  Fugier et al. .............. 585/600

*Primary Examiner*—Asok Pal
*Assistant Examiner*—P. Achutamurthy
*Attorney, Agent, or Firm*—Pennie & Edmonds

[57] ABSTRACT

A process for the preparation of undeca-1,3,5-triene, a prized perfuming ingredient, in two, respectively three, steps starting from sorbic acid, which makes it possible to obtain said compound in its undeca-1,3E,5Z preferred isomeric form, is disclosed.

9 Claims, No Drawings

PROCESS FOR THE PREPARATION OF AN UNSATURATED POLYOLEFIN

BRIEF SUMMARY OF THE INVENTION

The present invention relates to the perfume industry. It concerns in particular a process for the preparation of undeca-1,3,5-triene, wherein:

a. hexanal is added to the di-lithium salt of sorbic acid having the formula

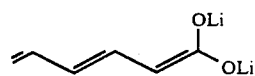

to obtain a β-hydroxylic acid of formula

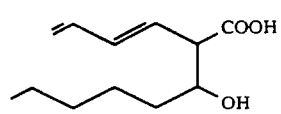

and b. said β-hydroxylic acid is subjected to an elimination reaction by way of a treatment with a reagent consisting of a N,N-dimethylformamide-dialkylacetal or of the adduct formed by triphenylphosphine and the diethyl ester of azodicarboxylic acid, or c. said β-hydroxylic acid is converted into the lactone of formula

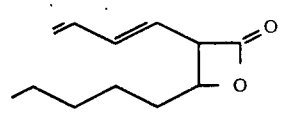

by treatment with acetyl chloride, acetic anhydride, methyl chloroformate, methylsulfonyl chloride or an arenesulfonyl chloride, in the presence of a base; and c. the thus obtained lactone is subjected to a thermal treatment at a temperature of between 250° and 300° C.

The invention further provides a method to confer, improve, enhance or modify the organoleptic properties of a perfuming or flavoring composition, or a perfumed or flavored article, which method comprises adding to said composition or article an effective amount of the undeca-1,3,5-triene obtained by the process described above.

Another object of the invention is the formula (II) acid, in its (1RS,2SR) or (1RS,2RS) form, as well as the lactone of formula (III) in its (3RS,4SR) or (3RS,4RS) form.

BACKGROUND OF THE INVENTION

There have been many proposed ways of synthesizing undeca-1,3,5-triene [see, for example, patent FR 74 19580; patent AS 68 01077; patent application EP 203 615; F. Naef et al., Helvetica Chimica Acta 1975, 58, 1016; V. Ratovelomanana et al.; Bull. Soc. Chim. Fr. 1987, 174; Recherches 1967, 16, 5; W. Boland et al., Helv. Chim. Acta 1987, 70, 1025; E. Block et al., J. Amer. Chem. Soc. 1986, 108, 4568] ever since its discovery [see: Chrétien-Bessière et al., Bull. Soc. Chim. Fr. 1967, 97]. Amongst the methods proposed, there are some which have found an industrial application and undeca-1,3,5-triene is presently commercialized under several tradenames. Since it is characterized by the presence of three ethylenic double bonds in its molecule, undeca-1,3,5-triene can take several isomeric forms, the respective proportions of which in the final product determine its olfactive quality. We have been able to establish that none of the described prior art methods can, at once, satisfy the economic, safety and environmental requirements and provide an irreproachable quality product, of better quality than that of the product currently available on the market.

The process of the present invention has the advantage of providing undeca-1,3,5-triene in the form of a mixture of isomers whose content in the undeca-1,3E,5Z-triene isomer is preponderant. It is precisely this isomer which best develops the most characteristic odor properties; its presence in the mixture thus improves the character of the latter.

THE INVENTION

The present invention thus provides a process for the preparation of undeca-1,3,5-triene as described above.

Said process can be illustrated by the following reaction scheme:

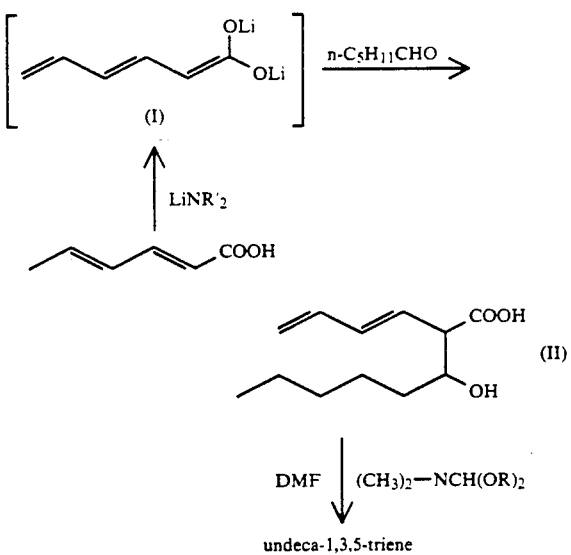

R and R' = alkyl or:

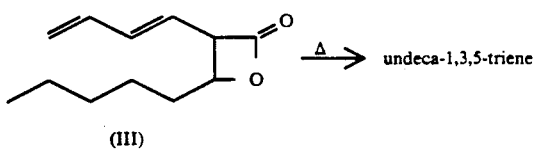

Ac = acetyl

As mentioned above, the main advantage of the process of the invention resides in the fact that it makes it possible to obtain undeca-1,3,5-triene in the form of a preferred isomeric mixture wherein the content in undeca-1,3E,5Z-triene is higher than the content in the 1,3E,5E isomer.

Such a result can be explained by the fact that the addition of hexanal on the di-anion formed by the di-lithium salt of sorbic acid (I) takes place in the α position to provide an anti/syn mixture of hydroxy-acid (II) wherein the respective ratio of the two isomers is a function of the temperature at which the addition reaction takes place.

Thus, low temperatures, for example around 0° C., favor the formation of the anti diastereomer, while higher temperatures, for instance of the order of 50° C., tend to promote the formation of the syn isomer:

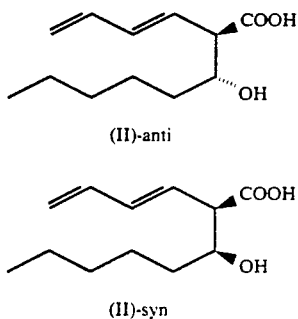

(II)-anti (II)-syn

Surprisingly, the formation of products resulting from an addition in the ε terminal position was not observed.

The following step of the process of the invention consists in a carboxy-hydroxylating elimination, which can be carried out by means of reagents known in the art for their capability to promote similar fragmentations [see, to this end: Hara et al., Tetrahedron Lett. 1975, 1545; Mulzer and Brüntrup, Angew. Chem. 1977, 89, 265; Mulzer and Lammar, Angew. Chem. 1983, 95, 629; Mulzer et al., J. Chem. Soc. Chem. Commun. 1979, 52; Rüttimann et al., Helv. Chim. Acta 1975, 58, 1450]. Such reagents include N,N-dimethylformamide-dialkylacetals, in particular N,N-dimethylformamide-dimethylacetal and N,N-dimethylformamide-dineopentylacetal, as well as the adduct consisting of the diethyl ester of azodicarboxylic acid with triphenylphosphine:

$EtO_2C-N=N-CO_2Et/Ph_3P$.

The fragmentation reaction is preferentially carried out in dimethylformamide.

According to a variant of the process of the invention, the β-hydroxylic acid (II), in the form of an anti-/syn mixture, is converted into the lactone (III) by way of a reaction with reagents such as an arenesulfonyl chloride, for example benzenesulfonyl chloride, an acidic chloride such as acetyl chloride, or acetic anhydride.

The lactonisation reaction is carried out in the presence of a base. It has been observed that upon use of a base such as a trialkylamine, for example triethylamine, there is formation of the lactone (III), preferentially in the form of an isomeric mixture wherein the proportion of cis isomer is preponderant (around 70:30). Furthermore, this proportion of the two isomers

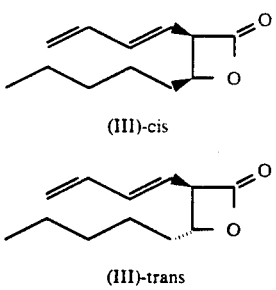

(III)-cis (III)-trans is independent of the respective anti/syn proportion of the starting β-hydroxylated acid. This result is all the more surprising when one considers that the literature discloses the highly syn-selective character of the lactonisation of β-hydroxylated acids by means of a benzenesulfonyl chloride/pyridine system [see references indicated above].

It has thus been possible to prepare lactone (III) in the form of an isomeric mixture having a 70:30 content, starting indifferently for example from a 2:1 or a 1:4 anti/syn mixture of the β-hydroxylic acid.

The last step of the process according to the described variant consists of a thermal treatment of the obtained lactone, which treatment can be carried out by the usual techniques, for example pyrolysis, at a temperature of between 250° and 300° C., preferably around 280° C., of the vapors of the lactone (III). A quartz pyrolysis tube is perfectly adequate for this operation. According to a preferred operation method, the lactone is previously dissolved in an appropriate solvent, for example ethyl acetate, under a flow of an inert gas such as nitrogen or argon, the vapors are pyrolyzed at 280° C. in a quartz tube of about 4 m length. The pyrolysate is then condensed to provide the desired undeca-1,3,5-triene, if necessary after purification and stabilization.

The di-lithium salt of sorbic acid (I), used as starting material in the process of the invention, can be obtained by treating sorbic acid with lithium diisopropylamide or with any other analogous reagent.

The β-hydroxylic acid (II), as well as the lactone (III), are compounds whose structure is novel. The present invention has also, as an object, these compounds, i.e.:

(1RS,2SR)-2-(1-hydroxyhexyl)-3,5-hexadienoic acid,
(1RS,2RS)-2-(1-hydroxyhexyl)-3,5-hexadienoic acid,
(3RS,4SR)-(E)-3-(1,3-butadienyl)-4-pentyl-2-oxetanone and
(3RS,4RS)-(E)-3-(1,3-butadienyl)-4-pentyl-2-oxetanone.

The present invention will be illustrated by way of the following examples wherein the temperatures are indicated in degrees centigrade and the abbreviations have the usual meaning in the art.

EXAMPLE

Method A a. A mixture consisting of the di-lithium salt of sorbic acid was prepared as follows.

In a 1.5 l flask, equipped with a mechanical stirrer and kept under argon, styrene (3.2 g; 0.031 mole) was quickly added at 38° to a suspension of lithium granulates (4.24 g; 0.606 mole) in 61.2 g (0.606 mole) of diisopropylamine and 400 ml of tetrahydrofuran (THF). After 10 min, once the reaction was triggered, a solution of styrene (28.4 g; 0.273 mole) in 200 ml of THF was added slowly over 45 min. Once the introduction was completed, the reaction mixture was heated at 38° for one hour more. The obtained solution was then cooled to −10° and 29.7 g (0.265 mole) of sorbic acid in 200 ml of THF were added thereto while maintaining the temperature below −2°.

After 15 min, 35.8 g (0.358 mole) of hexanal were added, over 20 min, to the reaction mixture while keeping the temperature between −10° and −2°. After 15 min, the cold reaction mixture was poured into ice-cold water (250 ml), then diluted with 150 ml of pentane, which allowed a good phase separation. The separated organic phase was washed with 200 ml of water and the combined aqueous layers were extracted with ether and acidified with 10% sulfuric acid (150 ml). After extracting twice with ether and washing the combined organic phases with water and an aqueous solution saturated with NaCl, the product was dried over $Na_2SO_4$, filtered and concentrated to give 56.1 g of a mixture of (1RS,2SR)-2-(1-hydroxyhexyl)-3,5-hexadienoic acid and (1RS,2RS)-2-(1-hydroxyhexyl)-3,5-hexadienoic acid (yield: 100%). Distillation of a 5 g sample of said mixture in a bulb-to-bulb apparatus, at 150°–190° (oven temp./1.33 Pa) provided 3.63 g (72%) of a mixture of the two acids whose content in isomer anti relative to the syn isomer was 2:1.

The (1RS,2SR) isomer presented the following analytical data:

IR($CHCl_3$): 3700–2400, 2930, 1700, 1400, 1275 $cm^{-1}$.

$^1$H-NMR(360 MHz): 0.88(3H, t, J=7); 1.17–1.62(8H, m); 3.12(1H, t, J=9); 3.86(1H, m); 5.12(1H, d, J=10); 5.22(1H, d, J=16); 5.65(1H, d×d, J=9 and 14.5); 6.25(1H, m); 6.32(1H, m); ~6.0–6.5(2H, broad) δ ppm.

$^{13}$C-NMR(360 MHz): 14.0(q); 22.6(t); 25.1(t); 31.7(t); 34.6(t); 56.0(d); 72.7(d); 118.1(t); 127.5(d); 135.5(d); 136.1(d); 177.6(s) δ ppm.

MS: 194(3), 123(11), 112(77), 97(78), 94(36), 81(35), 67(91), 55(65), 44(92), 41(100), 39(60).

The (1RS,2RS) isomer presented the following analytical data:

$^1$H-NMR(360 MHz): 3.12(d×d, 1H, J=13 and 3.5); 4.00(1H, m); 5.80(1H, d×d, J=9 and 14.5) δ ppm.

$^{13}$C-NMR(360 MHz): 25.3(t); 34.1(t); 71.9(d); 117.9(d); 126.1(d); 136.2(d); 136.4(d); 178.4(s) δ ppm.

b. 7.01 G (33.1 mmole) of the acids obtained as indicated above in solution in 50 ml of dimethylformamide (DMF) were added dropwise at 50° to a stirred solution of 4.34 g (4.85 ml; 36.4 mmole) of dimethylformamide-dimethylacetal in 20 ml of DMF. Once the introduction was completed (45 min), the evolution of $CO_2$ ceased and the reaction mixture was stirred for a further 15 min and then poured into a mixture of ice/water. After extracting three times with petroleum ether, the combined organic extracts were washed with water, with a 5% aqueous solution of HCl, with sodium bicarbonate and finally with an aqueous solution saturated with NaCl. Evaporation of the organic phase yielded 4.82 g of raw undeca-1,3,5-triene, which was stabilized by addition of BHA. A fractional distillation of this material gave a fraction having b.p. 80°−2°/1.06×10$^3$ Pa consisting of undeca-1,3,5-triene in its trans,cis-1,3,5- and trans,trans-1,3,5-undecatriene isomeric forms (58:42).

A mixture of the above-mentioned β-hydroxylic acids was prepared by following the method described above but, after adding the hexanal, the reaction mixture was heated at 50° for 3 h. The yield in the obtained acids was 100%. However, in this case, the respective content in the isomers anti/syn was 1:4.

Method B c. A solution of the β-hydroxylic acids obtained as indicated above (40.1 g; purity: ~80%) in 750 ml of toluene was treated at 0° with 57.3 g (79 ml; 567 mmole) of triethylamine. A solution of 11.9 g (10.75 ml; 151 mmole) of acetyl chloride in 25 ml of toluene was added over 45 min. The temperature was maintained at +2° and the mixture was stirred for 3 h, then 2.97 g (2.69 ml; 37.8 mmole) of acetyl chloride in 15 ml of toluene were added thereto. A last fraction, consisting of 1.49 g (1.35 ml; 18.9 mmole) of acetyl chloride in 10 ml of toluene was finally added to complete the reaction. After 30 min, 200 ml of water were added to the cold mixture, which was acidified with 100 ml of a 10% aqueous solution of $H_2SO_4$ and extracted with ether. The combined organic phases were washed with water, a 5% aqueous solution of NaOH, an aqueous solution saturated with NaCl and then dried over $Na_2SO_4$ and evaporated. After distillation (100°–180°/66.5 Pa), 18.49 g of a mixture of (3RS,4SR)-(E)-3-(1,3-butadienyl)-4-pentyl-2-oxetanone and (3RS,4RS)-(E)-3-(1,3-butadienyl)-4-pentyl-2-oxetanone (70:30; yield: 51%) were obtained. The two components of this mixture were separated by chromatography on a column filled with $SiO_2$ (eluting agent: cyclohexane/ethyl acetate: 95:5).

The analytical data of (3RS,4SR)-(E)-3-(1,3-butadienyl)-4-pentyl-2-oxetanone were as follows:

$^1$H-NMR(360 MHz): 0.90(3H, broad s); 1.20–1.80(8H, m); 4.38(1H, t, J=7); 4.60(1H, m); 5.19(1H, d, J=10); 5.09(1H, d, J=15); 5.64(1H, d×d, J=14.5 and 7); 6.35(2H, m) δ ppm.

$^{13}$C-NMR(360 MHz): 13.9(q); 22.4(t); 24.8(t); 31.0(t); 31.4(t); 55.7(d); 76.2(d); 119.3(t); 120.6(d); 135.6(d); 137.3(d); 169.6(s) δ ppm.

MS: 150(18), 91(32), 79(100), 66(45), 41(28).

The analytical data of (3RS,4RS)-(E)-3-(1,3-butadienyl)-4-pentyl-2-oxetanone were the following:

$^1$H-NMR(360 MHz): 0.90(3H, t, J=~7.3); 1.23–1.97(8H, m); 3.88(1H, d×d, J=8 and 4.5); 4.35(1H, d×d×d, J=7, 7 and 4.5); 5.18(1H, d, J=10); 5.27(1H, d, J=16); 5.73(1H, d×d, J=14.5 and 7); 6.30(2H, m) δ ppm.

$^{13}$C-NMR(360 MHz): 13.9(q); 22.4(t); 24.6(t); 31.4(t); 34.2(t); 59.1(d); 78.3(d); 119.2(t); 123.4(d); 135.6(d); 168.9(s) δ ppm.

MS: 150(16), 91(33), 79(100), 66(35), 41(22).

The IR spectrum of the mixture of the two lactones was the following: IR: 2925, 1810, 1680, 1600, 1460 $cm^{-1}$.

d. 18.49 G of the mixture of lactones obtained as indicated under c. in 210 ml of ethyl acetate were pyrolyzed in a quartz column of 4 m length under nitrogen pressure at 280° (flow: 1.3 ml/min). The pyrolysate, collected in a trap cooled with dry ice and acetone, was evaporated and the residue was treated with 100 mg of BHA and then distilled at 80°–82°/5.32×10$^2$ Pa. 9.88 G (yield: 69%) of undeca-1,3,5-triene, in the form of a 70:30 mixture of undeca-1,3E,5Z-triene and undeca-1,3E,5E-triene, were thus obtained.

What we claim is:

1. Process for the preparation of undeca-1,3,5-triene, wherein:
   a. hexanal is added to the di-lithium salt of sorbic acid having the formula

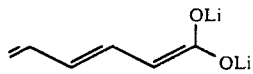

to obtain a β-hydroxylic acid of formula

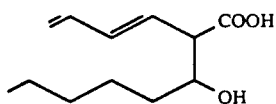

and b. said β-hydroxylic acid is subjected to an elimination reaction by way of a treatment with a reagent consisting of a N,N-dimethylformamide-dialkylacetal or of the adduct formed by triphenylphosphine and the diethyl ester of azodicarboxylic acid, or c. said β-hydroxylic acid is converted into the lactone of formula

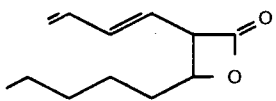

by treatment with acetyl chloride, acetic anhydride, methyl chloroformate, methylsulfonyl chloride or an arenesulfonyl chloride, in the presence of a base; and c. the thus obtained lactone is subjected to a thermal treatment at a temperature of between 250° and 300° C.

2. Process according to claim 1, wherein hexanal is added to the di-lithium salt of sorbic acid of formula (I) at a temperature below 10° C., preferably around 0° C., to give a β-hydroxylic acid whose content in isomer anti is preponderant.

3. Process according to claim 1, wherein hexanal is added to the di-lithium salt of sorbic acid of formula (I) at a temperature of about 50° C. to give a β-hydroxylic acid whose content in isomer syn is preponderant.

4. Process according to claim 1, wherein said N,N-dimethylformamide-dialkylacetal is N,N-dimethylformamide-dimethylacetal or N,N-dimethylformamide-dineopentylacetal.

5. Process according to claim 1, wherein said arenesulfonyl chloride is benzenesulfonylchloride.

6. Process according to claim 1, wherein the elimination reaction of step b. is carried out in dimethylformamide.

7. Process according to claim 1, wherein the conversion of said β-hydroxylic acid into the corresponding lactone, according to step c., is carried out in the presence of an organic base consisting of a tertiary amine.

8. Process according to claim 7, wherein said tertiary amine is triethylamine.

9. Process according to claim 1, wherein the thermal treatment of said lactone, according to step d., is carried out at around 280° C. under an inert gas atmosphere.

* * * * *